US011273330B2

(12) United States Patent
Warnking

(10) Patent No.: US 11,273,330 B2
(45) Date of Patent: *Mar. 15, 2022

(54) METHOD AND APPARATUS FOR PERFORMANCE OF THERMAL BRONCHIOPLASTY TO REDUCE COVID-19-INDUCED RESPIRATORY DISTRESS AND TREAT COVID-19-DAMAGED DISTAL LUNG REGIONS

(71) Applicant: AerWave Medical, Inc., Naples, FL (US)

(72) Inventor: Reinhard J. Warnking, Cologne (DE)

(73) Assignee: AerWave Medical, Inc., Naples, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/242,557

(22) Filed: Apr. 28, 2021

(65) Prior Publication Data

US 2021/0402218 A1  Dec. 30, 2021

Related U.S. Application Data

(63) Continuation of application No. 16/919,780, filed on Jul. 2, 2020, now Pat. No. 11,020,618.

(Continued)

(51) Int. Cl.
*A61N 7/00* (2006.01)
*A61N 7/02* (2006.01)
(Continued)

(52) U.S. Cl.
CPC ............... *A61N 7/02* (2013.01); *A61B 1/07* (2013.01); *A61B 1/2676* (2013.01);
(Continued)

(58) Field of Classification Search
CPC .............. A61N 7/02; A61N 2007/0004; A61N 2007/025; A61N 7/022; A61N 2007/0021;
(Continued)

(56) References Cited

U.S. PATENT DOCUMENTS

| 2003/0060813 A1 | 3/2003 | Loeb | A61B 18/24 606/17 |
| 2005/0222558 A1 | 10/2005 | Baxter | A61B 18/24 606/16 |

(Continued)

FOREIGN PATENT DOCUMENTS

WO  2012-120495  9/2012  ............... A61N 7/00

OTHER PUBLICATIONS

Nuvaira. "Minimally Invasive Procedure for COPD Treatment." Nuvaira, Dec. 26, 2019, web.archive.org/web/20191226085420/www.nuvaira.com/the-procedure/. Accessed Apr. 2, 2021. (Year: 2019).

(Continued)

*Primary Examiner* — Jaymi E Della
(74) *Attorney, Agent, or Firm* — R. Neil Sudol; Henry D. Coleman

(57) ABSTRACT

Apparatus and methods for deactivating pulmonary nerves extending along the main bronchi of a mammalian subject to reduce ARDS effects by advancing an ultrasound transducer into the right and subsequently left main bronchus. The ultrasound transducer emits circumferential ultrasound so as to heat a circumferential tissue volume encompassing the right and left main bronchus. The energy of <10 W acoustic for <5 sec will not be sufficient to cause tissue necrosis but sufficient to inactivate nerve conduction. This treatment can be performed without locating or focusing on individual pulmonary nerves.

15 Claims, 9 Drawing Sheets

Related U.S. Application Data

(60) Provisional application No. 63/043,933, filed on Jun. 25, 2020.

(51) Int. Cl.
*A61B 1/07* (2006.01)
*A61B 1/267* (2006.01)
*A61B 18/14* (2006.01)
*A61B 18/02* (2006.01)
*A61B 18/00* (2006.01)

(52) U.S. Cl.
CPC ...... *A61B 18/0206* (2013.01); *A61B 18/1492* (2013.01); *A61B 2018/0022* (2013.01); *A61B 2018/00541* (2013.01); *A61B 2018/00982* (2013.01); *A61B 2018/00994* (2013.01); *A61B 2018/0212* (2013.01); *A61N 2007/0004* (2013.01)

(58) Field of Classification Search
CPC .......... A61N 2007/003; A61B 18/0206; A61B 2018/00994; A61B 2018/00541
See application file for complete search history.

(56) References Cited

U.S. PATENT DOCUMENTS

| | | | |
|---|---|---|---|
| 2008/0287837 A1 | 11/2008 | Makin | A61B 18/06 601/2 |
| 2011/0144491 A1 | 6/2011 | Sliwa | A61B 8/085 600/439 |
| 2013/0103028 A1 | 4/2013 | Tsoref | A61N 7/022 606/41 |
| 2016/0008636 A1 | 1/2016 | Warnking | A61B 8/483 600/411 |
| 2016/0113699 A1 | 4/2016 | Sverdlik | A61N 7/00 606/27 |
| 2016/0220851 A1 | 8/2016 | Mayse | A61N 7/022 |
| 2016/0287912 A1 | 10/2016 | Warnking | A61B 8/08 |
| 2020/0238085 A1 | 7/2020 | Khodaparast | A61N 1/0492 |

OTHER PUBLICATIONS

Buehler, Markus J. "Nanomechanical sonification of the 2019-nCoV coronavirus spike protein through a materiomusical approach." Apr. 2, 2020, https://web.archive.org/web/20200402064158/https://arxiv.org/ftp/arxiv/papers/2003/2003.14258.pdf. Accessed Apr. 2, 2021. (Year: 2020).

Armitage, L., & Rachel, B. (Jun. 22, 2020). Inhaled corticosteroids: A rapid review of the evidence for treatment or prevention of COVID-19. Retrieved Aug. 20, 2020, from https://www.cebm.net/covid-19/inhaled-corticosteroids-a-rapid-review-of-the-evidence-for-treatment-or-prevention-of-covid-19/ (Year: 2020).

M. C. (Apr. 24, 2020). Turning up the heat on COVID-19: Heat as a therapeutic intervention. Retrieved Aug. 20, 2020, from https://f1000research.com/articles/9-292/v1 (Year: 2020).

Q&A: Dexamethasone and COVID-19. (Jun. 25, 2020). Retrieved Aug. 20, 2020, from https://www.who.int/news-room/q-a-detail/q-a-dexamethasone-and-covid-19 (Year: 2020).

Zurn, R. (May 28, 2020). Ultrasound may prove to be effective, noninvasive treatment for COVID-19. Retrieved Aug. 20, 2020, from https://cse.umn.edu/college/feature-stories/ultrasound-may-prove-be-effective-noninvasive-treatment-covid-19 (Year: 2020).

Marcela, M. (May 18, 2020). The Use of Core Warming as a Treatment for Coronavirus Disease 2019 (COVID-19): An Initial Mathematical Model. Retrieved Aug. 20, 2020, from https://jca.emnuvens.com.br/jca/article/view/3382/3396 (Year: 2020).

Xu, Z., et al., (Feb. 18, 2020). Pathological findings of COVID-19 associated with acute respiratory distress syndrome. Retrieved Aug. 20, 2020, from https://www.sciencedirect.com/science/article/pii/S221326002030076X?via=ihub (Year: 2020).

METHOD AND APPARATUS FOR PERFORMANCE OF THERMAL BRONCHIOPLASTY TO REDUCE COVID-19-INDUCED RESPIRATORY DISTRESS AND TREAT COVID-19-DAMAGED DISTAL LUNG REGIONS

CROSS REFERENCE TO RELATED APPLICATIONS

This application is a continuation of application Ser. No. 16/919,780 filed Jul. 2, 2020, now U.S. Pat. No. 11,020,618. This application also claims the benefit of U.S. Provisional Patent Application No. 63/043,933 filed Jun. 25, 2020.

FIELD OF THE INVENTION

This application relates to a method and related apparatus for mitigating the effects of ARDS (Acute Respiratory Distress Syndrome). More particularly, the present invention contemplates the use of bronchioplasty to mitigate ARDS.

BACKGROUND OF THE INVENTION

As the COVID 19 pandemic made painfully clear ARDS can be a fatal respiratory issue. There are no successful treatments currently known other than to increase the oxygen supply with ventilators for the patient.

Increased mucus production, airway inflammation and smooth muscle contraction resulting in airway obstruction would amplify ARDS and have to be avoided. This obstruction can be treated by injuring and scaring the bronchial walls. This remodeling of the bronchial walls stiffens the bronchia and reduces contractility. Mechanical means and heat application have been proposed as in U.S. Pat. No. 8,267,094 B2. Other approaches focus on destruction of smooth muscle cells surrounding the bronchia as described in U.S. Patent Application Publication No. 2012/0143099A1 and U.S. Pat. No. 7,906,124B2. Others describe applying RF energy to the bronchial wall and thereby directly widening the bronchia through a process which is not disclosed as in U.S. Pat. Nos. 7,740,017B2 and 8,161,978B2. Whatever the process, the bronchial wall will be damaged and the procedure therefore has to be staged as described in U.S. Pat. No. 7,740,017B2. European Patent No. 2405841 describes applications of heat shocks through infused agents.

Inactivating conduction of the nerves surrounding the bronchia has been proposed in U.S. Patent Application Publication No. US2012/0203216A1 through mechanical action i.e. puncturing, tearing, cutting nerve tissue. In U.S. Patent Application Publication No. 2011/0118 nerve tissue ablation is proposed by applying energy (RF, HIFU, Microwave, Radiation and Thermal Energy) directly to the nerves percutaneously. It is not taught how to identify the nerve location in order to align the energy focal point (i.e. HIFU) with the nerve location. This is an issue since nerves are too small to be visualized with standard ultrasound, CT or MRI imaging methods. Therefore, the focal point of the energy field cannot be predictably aligned with the target or nerve location. U.S. Pat. No. 8,088,127B2 teaches to denervate by applying RF energy to the bronchial wall with the catheter positioned inside the bronchial lumen. It is proposed to protect the bronchial wall through simultaneous cooling of the wall. This is of course a very time intensive treatment approach since the RF ablation is limited to the electrode contact area. Therefore numerous ablation zones need to be pieced together to obtain a larger ablation zone with increased probability of affecting nerves. Efficacy might be severely limited due to the cooling action.

However, how to selectively target predominantly nerves without affecting bronchial wall and surrounding tissue in a quick 5 to 10 min procedure even tolerated by a critically ill patient is not taught. There is a need for a device and method to selectively ablate bronchial nerves without causing damage to bronchial walls and surrounding tissues. If this can be achieved, treatments would be much easier and faster to perform. Today's multiple treatments (see U.S. Pat. No. 7,740,017B2 and Alair System description, BSX) could be reduced to a one time treatment much better tolerated by the critically ill patient suffering from ARDS.

SUMMARY OF THE INVENTION

The present invention contemplates the use of bronchioplasty to mitigate the effects of ARDS (Acute Respiratory Distress Syndrome). While with denervation the root cause of ARDS (thickened epithelium in the alveoli) is not cured the remaining healthy lung capacity can be fully utilized by performing denervation as described in International Patent Application Publication No. 2015/066 424 to prevent bronchial constriction enhancing the ARDS effects. In addition distal bronchioplasty in the affected lung regions with pulsed ultrasound is used to create shockwaves that cause mechanical stress through cavitation and therewith break up or remodel (create micro pores) endothelial thickening in the alveoli.

One aspect of the invention provides an apparatus for inactivating parasympathetic, efferent, bronchial nerve conduction in a human or non-human mammalian subject. The apparatus according to this aspect of the invention preferably includes an ultrasound transducer adapted for insertion into the bronchial system of the mammalian subject. The apparatus according to this aspect of the invention desirably also includes an actuator which is electrically connected to the transducer. The actuator most preferably is adapted to control the ultrasound transducer to transmit ultrasound energy into an circular impact volume of approximately 5 $cm^3$, encompassing the bronchial tube so that the circumferentially emitted ultrasound energy is applied at a therapeutic level sufficient to inactivate conduction of bronchial nerves throughout the impact volume. Such therapeutic level is below the level required for tissue ablation. Research has shown that temperatures as low as 50 C for about 10 sec are sufficient to permanently interrupt nerve conduction without causing tissue damage (Mechanisms of Phrenic Nerve Injury During RF Ablation at the Pulmonary Vein Orfice; Bunch, . . . , Packer).

Because the impact volume is relatively large, and because the tissues throughout the impact volume preferably reach temperatures of less than 55° C. sufficient to inactivate nerve conduction but no tissue necrosis, the preferred methods according to this aspect of the invention can be performed successfully without determining the actual locations of the bronchial nerves, and without targeting or focusing on the bronchial nerves. The treatment can be performed without measuring the temperature of tissues. Moreover, the treatment is performed without causing injury to the bronchi or surrounding tissue.

The apparatus may further include a catheter with a distal end and a proximal end, the transducer being mounted to the catheter adjacent the distal end, the transducer being constructed and arranged inside a compliant balloon which will make contact with the bronchial wall. This compliant balloon is filled with a circulating cooling fluid to conduct ultrasound energy from the transducer to the bronchial walls and surrounding tissue and nerves. This cooling fluid also transports excessive heat away from the transducer. About half of the electrical energy supplied to the transducer is converted into heat while the other half is converted to ultrasonic energy. The catheter has a expansible element, for example a compliant balloon, mounted adjacent the distal end. For example, the transducer may be adapted to transmit the ultrasound energy in a 360° cylindrical pattern surrounding a transducer axis, and the catheter may be constructed and arranged to hold the axis of the transducer generally parallel to the axis of the bronchial tube.

A further aspect of the invention provides methods for inactivating bronchial nerve conduction in a mammalian subject. A method according to this aspect of the invention desirably includes the steps of inserting an ultrasound transducer into a bronchial branch of the subject and actuating the transducer to transmit therapeutically effective ultrasound energy into an impact volume of approximately 5 cm$^3$ encompassing the bronchial branch. The ultrasound energy desirably is applied so that the therapeutically effective ultrasound energy of about 10 W (adjusted for bronchial diameter as described in prov. 003) inactivates conduction of all the nerves in the impact volume. For example, the step of actuating the transducer may be so as to maintain the temperature of the bronchial wall below 55° C. while heating the solid tissues within the impact volume, including the renal nerves in the impact volume, to above 50° C.

Because the impact volume is relatively large, and because the tissues throughout the impact volume preferably reach temperatures of 50° to 55° C. sufficient to inactivate nerve conduction, the preferred methods according to this aspect of the invention can be performed successfully without determining the actual locations of the bronchial nerves, and without targeting or focusing on the bronchial nerves. The treatment can be performed without measuring the temperature of tissues. Moreover, the treatment preferably is performed without causing injury to the bronchi or surrounding tissue. The preferred methods and apparatus can inactivate relatively long segments (>0.6 cm) of the bronchial nerves, so as to reduce the possibility of nerve recovery which would re-establish conduction along the inactivated segments.

A further aspect of the invention includes the steps of advancing the bronchoscope distally into by Covid 19 affected areas of the lung and inserting the ultrasound catheter through the working channel of the bronchoscope, inflating the compliant balloon with cooling and coupling fluid, ensuring circumferential wall contact through a diagnostic detection mode and applying pulsed ultrasound (for example 10 MHz pulsed with several KHz or KHz pulsed for several seconds) to the distal portions of the lung and therewith breaking up endothelial thickening in the alveoli.

Accordingly, a Covid-19 treatment method pursuant to the present invention comprises (i) inserting a distal portion of a bronchoscope into a bronchial tree of a Covid-infected subject distal to the main bronchial bifurcation, (ii) advancing an ultrasound catheter through a working channel of the bronchoscope into one of a left and right main bronchus, (iii) inflating a compliant balloon at a distal end of the ultrasound catheter with a cooling and coupling liquid so that the balloon enters into contact with a bronchial wall, (iv) operating a contact detector to determine whether contact is achieved, and (v) energizing an ultrasonic transducer at the distal end of said ultrasound catheter to apply circumferential focused or unfocused ultrasound energy at a sub-necrotic intensity of less than 10 W for less than 10 sec, thereby causing tissue heating of 50° to 55° C. for less than 10 sec at least deactivate nerves. The energizing the ultrasonic transducer at the distal end of said ultrasound catheter to apply circumferential focused or unfocused ultrasound energy includes energizing the ultrasonic transducer in pulses of predetermination duration and predetermined inter-pulse spacing, thereby pulsing the focused or unfocused ultrasound energy to induce mechanical stress in Covid affected lung segments in alveoli of the subject and breaking up or modifying a lung epithelial layer of the subject by virtue of the application of pulsed ultrasound energy.

Further aspects of the invention provide probes which can be used in the method and apparatus discussed above, and apparatus incorporating means for performing the steps of the methods discussed above.

DETAILED DESCRIPTION

Apparatus according to one embodiment of the invention (FIG. 2) is advanced through the working channel of a bronchoscope 5. Alternatively, the catheter can be advanced through a sheath. The sheath generally may be in the form of an elongated tube having a proximal end, a distal end and a proximal-to-distal axis. As used in this disclosure with reference to elongated elements for insertion into the body, the term "distal" refers to the end which is inserted into the body first, i.e., the leading end during advancement of the element into the body, whereas the term "proximal" refers to the opposite end. The sheath may be a steerable sheath. Thus, the sheath may include known elements such as one or more pull wires (not shown) extending between the proximal and distal ends of the sheath and connected to a steering control arranged so that actuation of the steering control by the operator flexes the distal end of the sheath in a direction transverse to the axis. The sheath might be equipped with a circular ultrasound imaging array at the distal portion to allow for image guidance for the denervation procedure (as described in detail in 61/770,810)

Figure 4A:
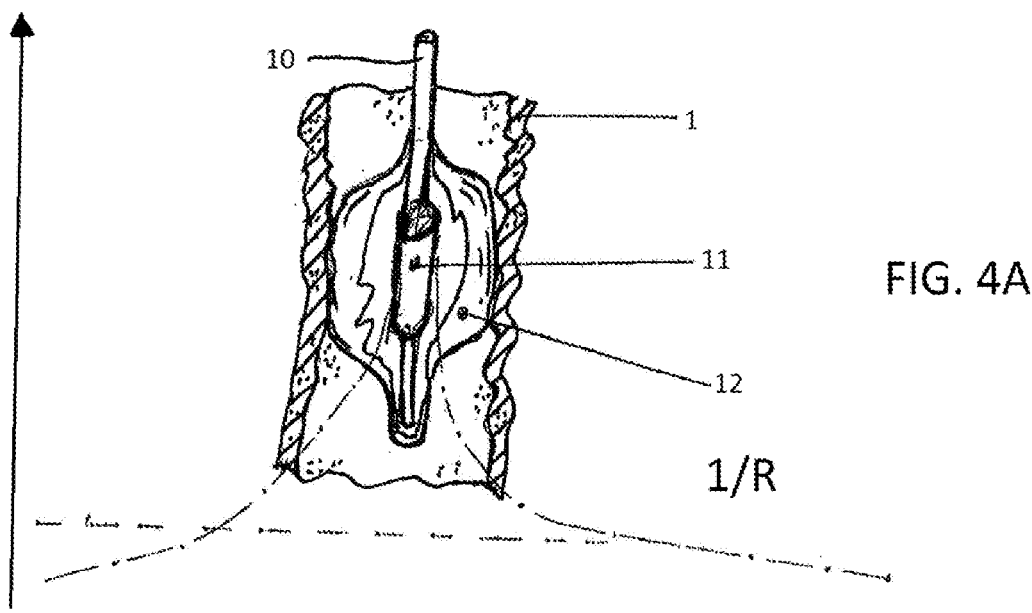
FIGS. 4A and 4B are longitudinal cross-section views of a bronchial tube showing an ultrasound treatment transducer and schematically demonstrating the effects on power distribution of proper alignment vs. a non-centered, non-aligned ultrasound transducer
Figure 4B:
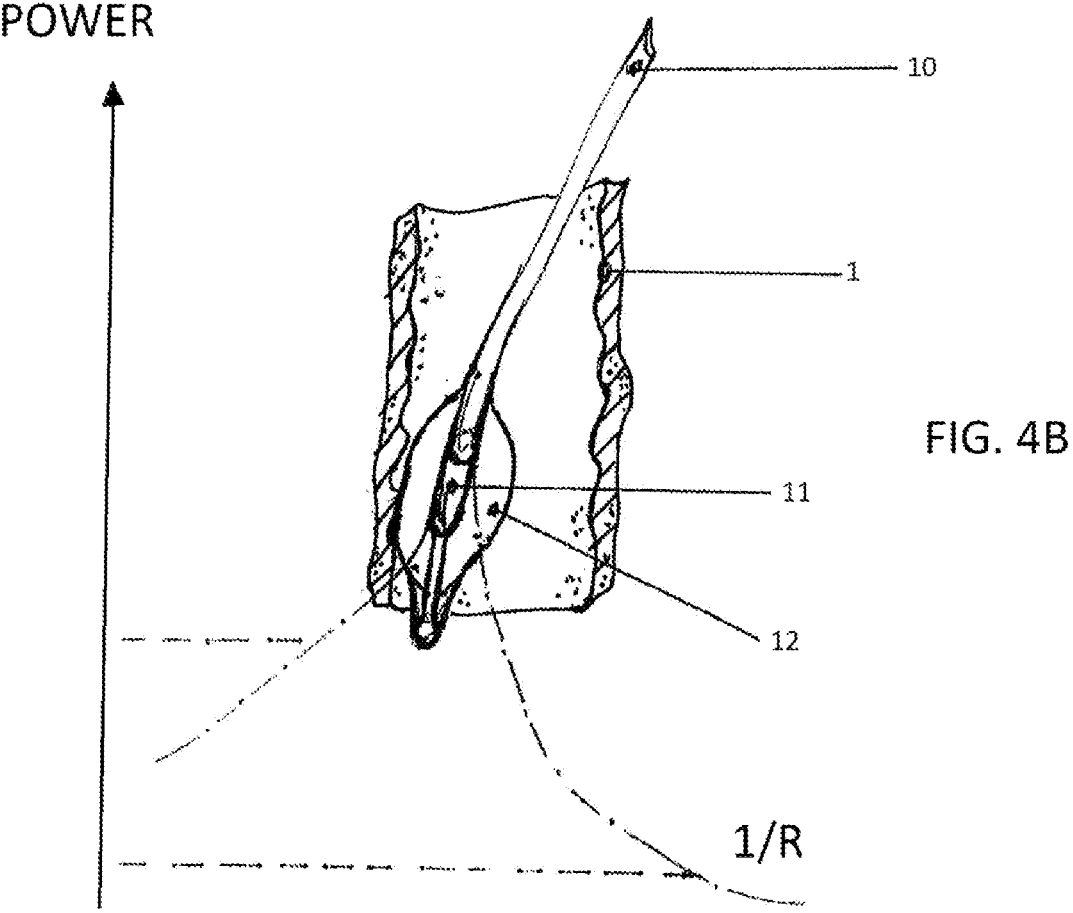
Figure 5:
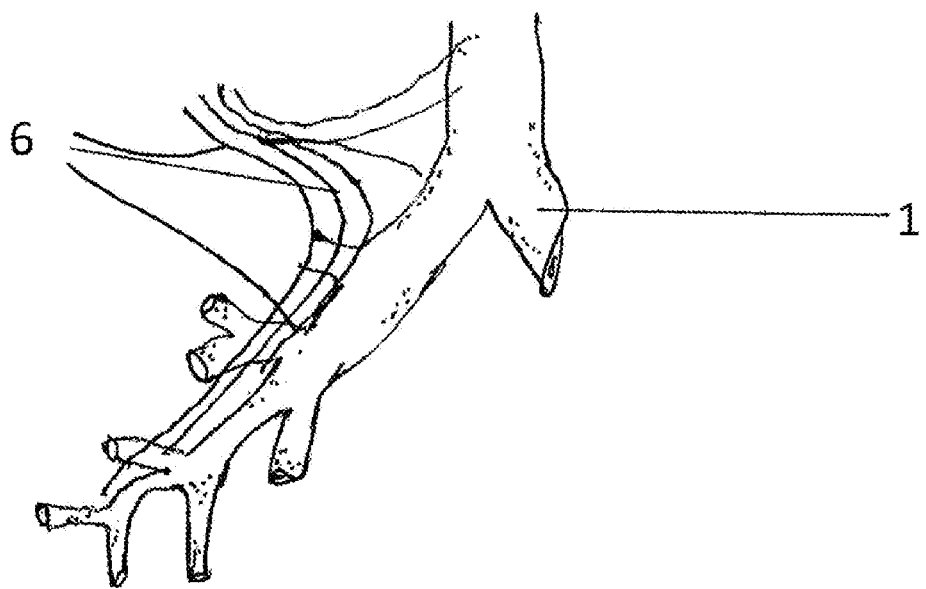
FIG. 5 shows a right bronchial branch with adjacent nerves running alongside the bronchial tube.
Figure 6:
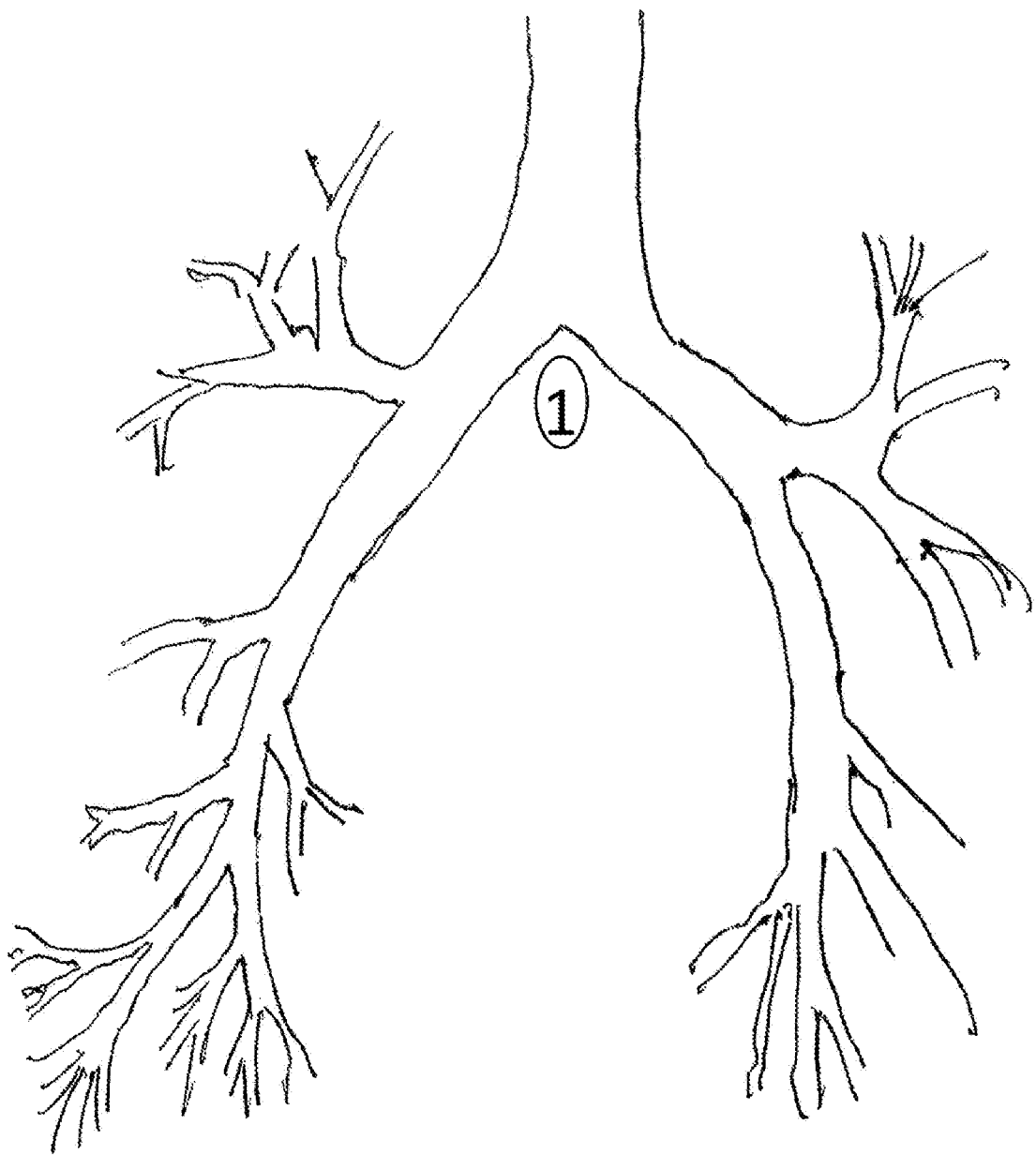
FIG. 6 shows a bronchial tree in its entirety.

The apparatus also includes a catheter 10 having a proximal end, a distal end and a proximal-to-distal axis which, in the condition depicted in FIG. 4 is preferably coincident with the bronchial axis. Alignment with the bronchial axis will provide for a more homogeneous energy distribution through the treatment volume (see upper diagram in FIG. 4). In the case of miss alignment the energy levels vary greatly from side to side as shown in the lower diagram of FIG. 4. This will cause wall injury on one side while the other side is ineffective in ablating nerves. Centering will cause the flatter portion of the 1/r curve to determine the energy distribution within the treatment volume and therewith a more homogeneous energy- and therewith temperature distribution as shown in the upper diagram of FIG. 4.

Figure 8:
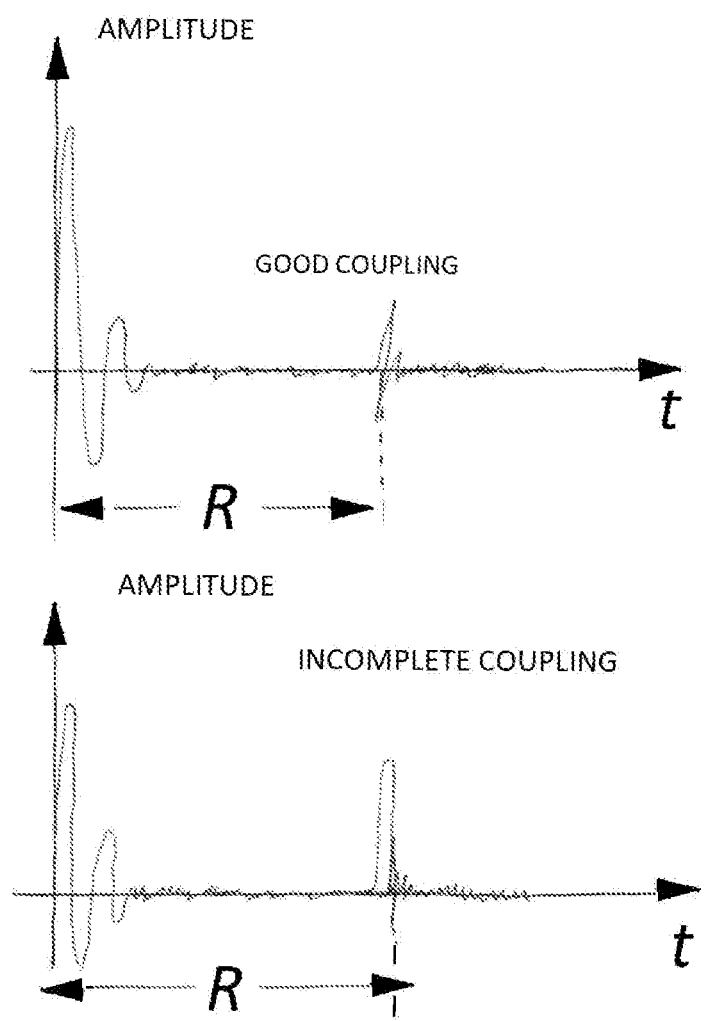
FIG. 8 is pair of graphs describing the receive mode of an ultrasonic transducer acting as coupling detector, showing amplitude of sensed ultrasound waves as a function of time.

Catheter 10 has a compliant balloon 12 mounted at the distal end. In its inflated condition (FIGS. 2 and 3), balloon 12 will engage the bronchial wall and therewith allow for ultrasound to be conducted from the transducer into the bronchial wall and surrounding tissues. Circumferential contact is ensured through a diagnostic coupling detection as outlined in FIG. 8. After emitting a short 10 MHz burst of ultrasound the actuator is switched into receive mode to monitor reflected echo signals. If there is insufficient coupling of the balloon with the bronchus, trapped air will cause a large echo as shown in the lower trace of FIG. 8. After coupling has been improved by further balloon inflation only a small echo representing the fluid/tissue impedance change is recorded as shown in the upper trace of FIG. 8.

An ultrasound transducer 11 (FIG. 3) is mounted adjacent the distal end of catheter 10 within balloon 12. Transducer 11, which is desirably formed from a ceramic piezoelectric material, is of a tubular shape and has an exterior emitting surface in the form of a cylindrical surface of revolution about the proximal-to-distal axis of the transducer 11. The transducer 11 typically has an axial length of approximately 2-10 mm, and preferably 6 mm. The outer diameter of the transducer 30 is approximately 1.5-3 mm in diameter, and preferably 2 mm to allow for insertion of the ultrasound catheter through a working channel of a bronchoscope. The transducer 11 also has conductive coatings (not shown) on its interior and exterior surfaces. Thus, the transducer may be physically mounted on a metallic support tube which in turn is mounted to the catheter shaft. The coatings are electrically connected to ground and signal wires. Wires extend from the transducer 11 through a lumen in the catheter shaft to a connector electrically coupled with the ultrasound system. The lumen extends between the proximal end and the distal end of a catheter 10, while the wires extend from the transducer 11, through the lumen, to the proximal end of the catheter 10.

Transducer 11 is arranged so that ultrasonic energy generated in the transducer is emitted principally from the exterior emitting surface. Thus, the transducer may include features arranged to reflect ultrasonic energy directed toward the interior of the transducer so that the reflected energy reinforces the ultrasonic vibrations at the exterior surface. For example, support tube and transducer 11 may be configured so that the energy emitted from the interior surface of the transducer 11 is reflected back to enhance the overall efficiency of the transducer. In this embodiment, the ultrasound energy generated by the transducer 11 is reflected at the interior mounting to reinforce ultrasound energy propagating from the transducer 11, thereby ensuring the ultrasound energy is directed outwardly from an external surface of the transducer 11.

Figure 9:
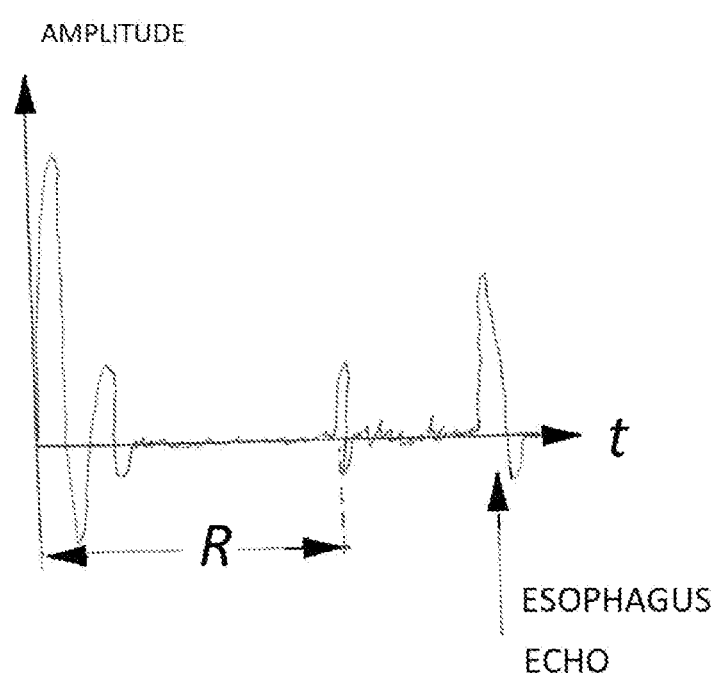
FIG. 9 is a graph, showing amplitude of sensed ultrasound waves as a function of time for use in determination of esophageal distance in receive mode.

Transducer 11 is also arranged to convert ultrasonic waves impinging on the exterior surface into electrical signals on wires. If the reflecting structure, for example the bronchial tube, is not perfectly circular the widths of the reflected signal will represent the difference between d max and d min (as described in detail in prov. xxxx 003). Besides measuring the bronchial diameter and adjusting the ultrasound energy accordingly the receive mode can also act as a coupling detector as described in FIG. 8. As shown in the upper diagram of FIG. 8 the balloon/bronchial wall interface will create a noticeable echo due to the impedance change. If coupling is incomplete air will be trapped between balloon and bronchial wall creating a significantly larger echo (see lower graph in FIG. 8). In this case the balloon will be further inflated until all air pockets or the respective echoes are gone. FIG. 9 describes the measurement of esophageal distance by analyzing the received echoes of an air filled space. In case the esophagus contains air intensity hot spots and potentially injury could be caused in the esophageal wall. If such an echo is being detected the treatment balloon needs to be advanced more distal in the main bronchus to increase the distance from the esophagus. In its simplest form transducer 11 is a circular ceramic tube with inner and outer electrodes not providing angular spatial resolution but only distance information. Stated another way, transducer 11 can act either as an ultrasonic emitter or an ultrasonic receiver. The receiving mode is of particular importance for an array type transducer as described in provisional application 61/770,818 because with an array type transducer 11 the received echoes can be resolved angularly (electronic focusing) and high resolution images can be achieved.

The transducer 11 is designed to operate, for example, at a frequency of approximately 1 MHz to approximately a few tens of MHz, and typically at approximately 10 MHz. The actual frequency of the transducer 11 typically varies somewhat depending on manufacturing tolerances. The optimum actuation frequency of the transducer may be encoded in a machine-readable or human-readable element (not shown) such as a digital memory, bar code or the like affixed to the catheter. Alternatively, the readable element may encode a serial number or other information identifying the individual catheter, so that the optimum actuation frequency may be retrieved from a central database accessible through a communication link such as the internet.

An ultrasound system also referred to herein as an actuator, is releasably connected to catheter 10 and transducer 11 through a plug connector. The control unit and ultrasound source are arranged to control the amplitude and timing of the electrical signals so as to control the power level and duration of the ultrasound signals emitted by transducer 11. The excitation source is also arranged to detect electrical signals generated by transducer 11 and appearing on wires and communicate such signals to the control unit.

A circulation device is connected to lumens (not shown) within catheter 10 which in turn are connected to balloon 12. The circulation device is arranged to circulate a liquid, preferably an aqueous liquid, through the catheter 10 to the transducer 11 in the balloon 12. The circulation device may include elements such as a tank for holding the circulating coolant, pumps, a refrigerating coil (not shown), or the like for providing a supply of liquid to the interior space of the balloon 12 at a controlled temperature, desirably at or below body temperature. The control board interfaces with the circulation device to control the flow of fluid into and out of the balloon 12. For example, the control board may include motor control devices linked to drive motors associated with pumps for controlling the speed of operation of the pumps.

Such motor control devices can be used, for example, where the pumps are positive displacement pumps, such as peristaltic or syringe pumps. Alternatively or additionally, the control circuit may include structures such as controllable valves connected in the fluid circuit for varying resistance of the circuit to fluid flow (not shown). The ultrasound system may further include pressure sensors, to monitor the liquid flow through the catheter 10. At least one pressure sensor monitors the flow of the liquid to the distal end of catheter 10 to determine if there is a blockage while the other monitors leaks in the catheter 10. While the balloon is in an inflated state, the pressure sensors maintain a desired pressure in the balloon preferably so that the compliant balloon occludes the bronchus.

The ultrasound system incorporates a reader for reading a machine-readable element on catheter 10 and conveying the information from such element to the control board. As discussed above, the machine-readable element on the catheter may include information such as the operating frequency and efficiency of the transducer 11 in a particular catheter 10, and the control board may use this information to set the appropriate frequency and power for exciting the transducer. Alternatively, the control board may be arranged to actuate an excitation source to measure the transducer operating frequency by energizing the transducer at a low power level while scanning the excitation frequency over a pre-determined range of frequencies for example 8.5 Mhz to 10.5 Mhz, and monitoring the response of the transducer to such excitation and to select the optimal operating frequency.

The ultrasonic system may be similar to that disclosed in U.S. Provisional Patent Application No. 61/770,818 filed Feb. 28, 2013, entitled "ULTRASOUND IMAGE GUIDED PERCUTANEOUS TRANS CATHER THERAPY," the disclosure of which is incorporated by reference herein.

Figure 1:
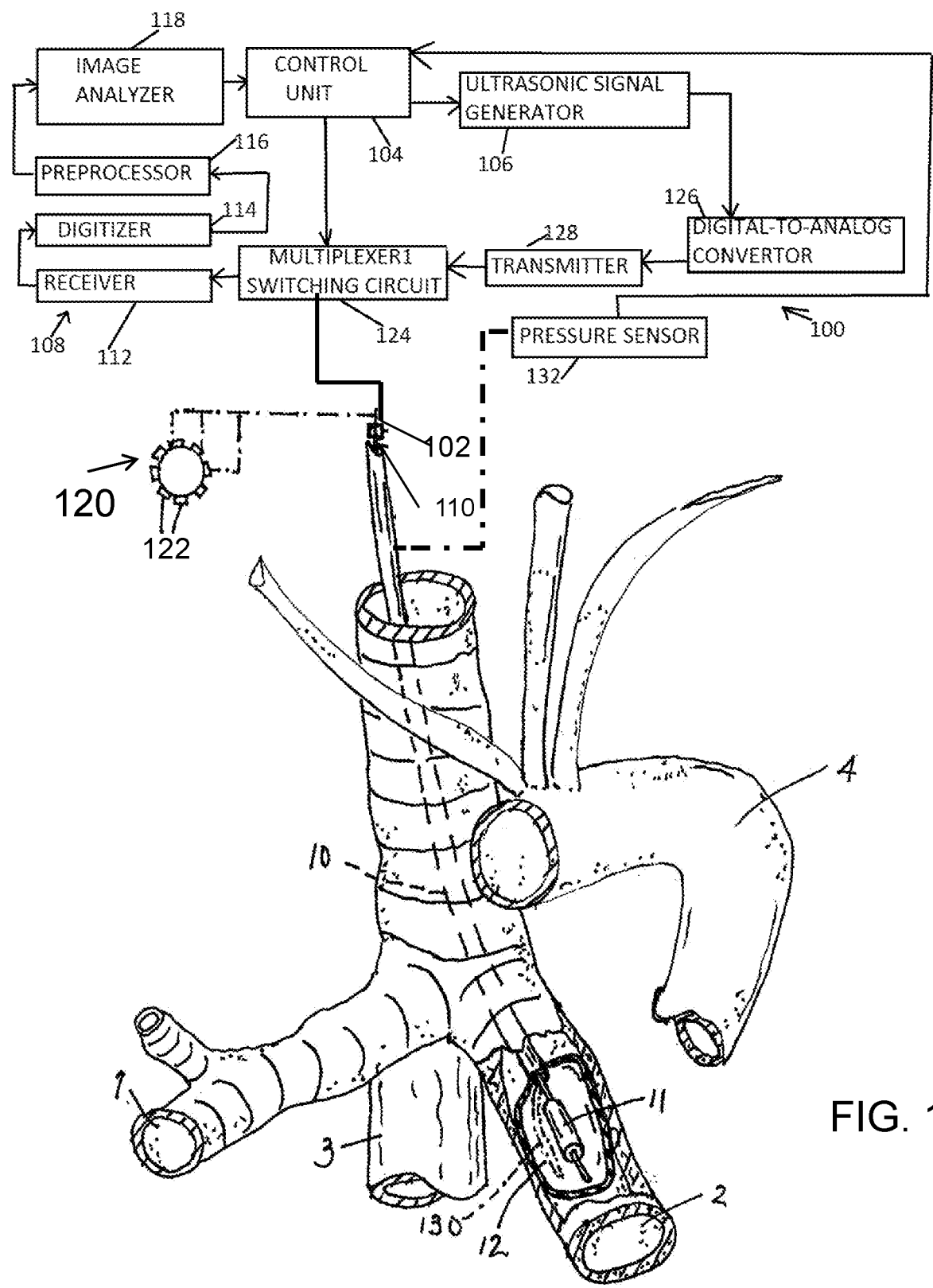
FIG. 1 is an anatomical view of typical main bronchial trunks 1 and 2 and associated structures.
Figure 7:
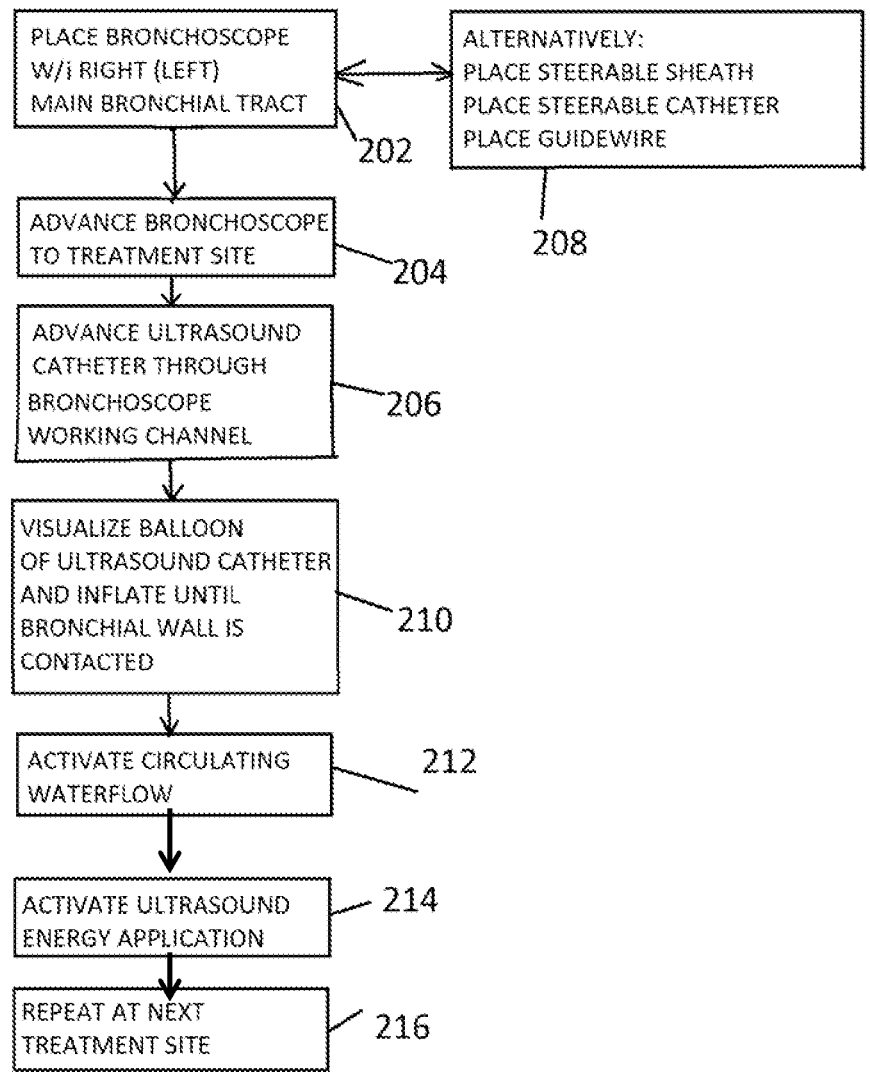
FIG. 7 is a flow chart depicting the steps used in treating the bronchi.

A method according to an embodiment of the present invention is depicted in flowchart form in FIG. 7. After preparing a human or non-human mammalian subject such as a patient (preparation of an tracheal access site), and connecting the catheter 10 to the ultrasound system, the ultrasound catheter 10 is inserted into the working channel of the bronchoscope after the bronchoscope has been advanced to the desired treatment site under visual guidance through the bronchoscope camera or optical fiber. Alternatively, a steerable sheath, preferably with ultrasound imaging capability as described in Prov 61/770,810, can be used as a delivery channel for the treatment catheter. In another embodiment the treatment catheter is equipped with a steering or deflection mechanism and can be advanced directly to the treatment site as shown in FIG. 1. The sheath or the ultrasound catheter might be inserted into the bronchus through a special laryngoscope. If the catheter combines imaging and therapeutic capabilities as described in the 818 prov., this delivery method enables the fastest procedure time and is easily tolerated by the patient. Alternatively to visual guidance with an optical fiber the treatment catheter position is controlled through depth markings on the catheter shaft, providing the insertion depth in comparison to pre procedural images as described in detail in prov. 003. Yet another embodiment provides for a guide wire 14 (in FIG. 2) to be delivered through the working channel of the bronchoscope to the treatment site and the ultrasound treatment catheter to be advanced over the wire after the bronchoscope has been withdrawn. This technique will allow for very small, flexible bronchoscopes to be utilized.

Figure 2:
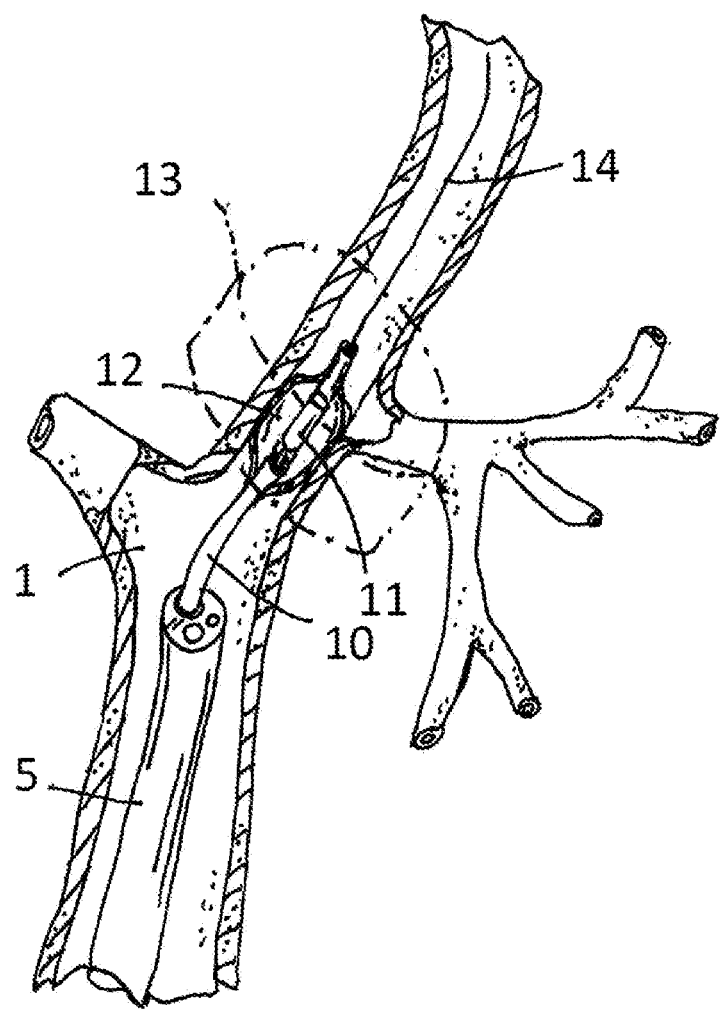
FIG. 2 is a diagram showing a treatment catheter 10 advanced through a bronchoscope (5) into the right bronchial branch and the diagrammatic sectional view depicting an ultrasound treatment volume (13).
Figure 3:
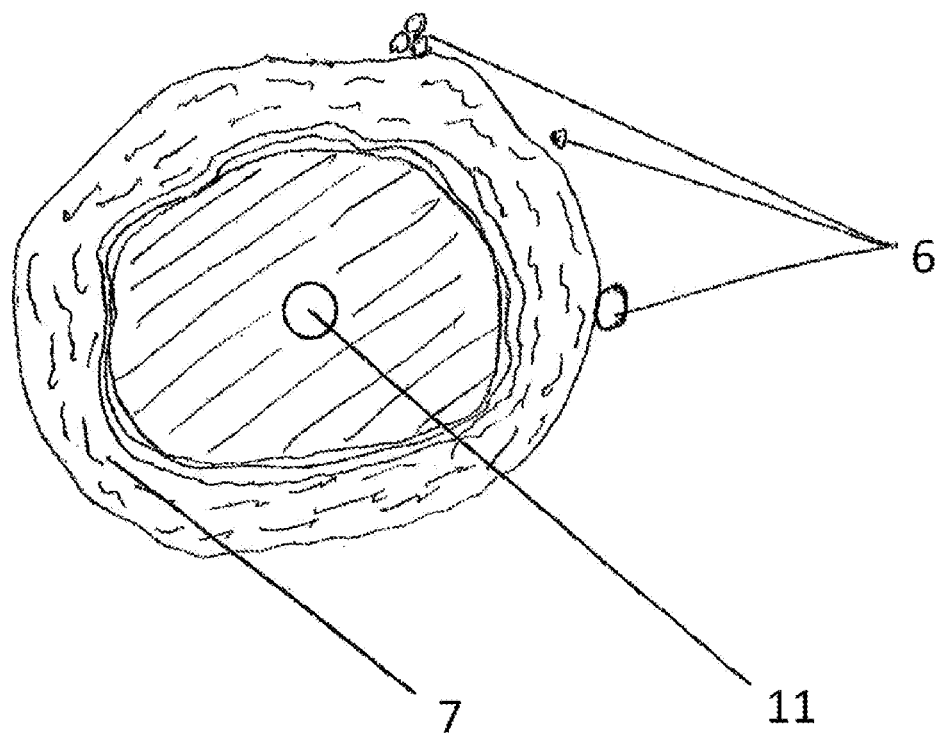
FIG. 3 shows a cross section through a bronchial tube with an ultrasound transducer (11) in the center surrounded by the cooling and coupling fluid in a compliant balloon.

Once the distal end of the catheter is in position within a bronchial branch pumps bring balloon 12 to an inflated condition as depicted in FIGS. 2 and 3. In this condition, the compliant balloon 12 engages the bronchial wall, and thus centers transducer 11 within the bronchial branch, with the axis of the transducer 11 approximately coaxial with the axis of the bronchial branch (see FIG. 4). This not only provides for a relatively homogeneous energy distribution circumferentially, but also keeps the very high energy levels close to the transducer located inside the cooling fluid where they are harmless, since ultrasound does not interact with the coupling/cooling fluid. If these peak energy levels where allowed to be located close to the bronchial wall (1), injury would result. These two situations are shown in FIG. 4 where in the upper drawing the ultrasound transducer is properly centered and the energy is distributed without causing wall (1) injury. The other advantage of proper centering is that the treatment volume is coinciding with the relatively flat portion of the 1/r curve providing an almost constant power level throughout the treatment volume. In the lower drawing of FIG. 4 the transducer is not centered resulting in uneven power distribution circumferentially. Also, the transducer is positioned off axis (due to too small a balloon diameter) which exposes the bronchial wall to a peak power level which may cause wall injury.

During treatment, the circulation device maintains a flow of cooled aqueous liquid into and out of balloon 12, so as to cool the transducer 11. The cooled balloon also tends to cool the interior surface of the bronchus.

The above-described method may be used in the treatment of acute respiratory distress syndrome (ARDS). In that case, the method further includes inactivating bronchial nerve conduction in a mammalian subject by virtue of the energizing the ultrasonic transducer at the distal end of said ultrasound catheter to apply circumferential focused or unfocused ultrasound energy, thereby reducing negative effects of ARDS and optimizing utilization of the remaining healthy lung capacity.

The above-described method may be used further in the treatment of Covid-19 respiratory disease. In particular, the energizing the ultrasonic transducer at the distal end of said ultrasound catheter to apply circumferential focused or unfocused ultrasound energy includes pulsing the focused or unfocused ultrasound energy. The method then entails inducing mechanical stress in Covid 19 affected lung segments in alveoli and breaking up or modifying a lung epithelial layer by virtue of the application of pulsed ultrasound energy.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

I claim:
1. A COVID-19 treatment method comprising:
  inserting a distal portion of an elongate introducer instrument into a bronchial tree of a subject diagnosed as having at least one COVID-19-damaged distal lung region;
  advancing an ultrasound catheter through a working channel of said elongate introducer instrument;
  disposing a distal end portion of said ultrasound catheter in a distal portion of the bronchial tree proximate the at least one COVID-19 damaged distal lung region;

inflating a compliant balloon at a distal end of the ultrasound catheter with a cooling and coupling liquid so that the balloon enters into contact with a bronchial wall of the subject proximate the at least one COVID-19 damaged distal lung region;

operating a contact detector to determine whether circumferential contact of the balloon with the bronchial wall of the subject is achieved; and thereafter energizing an ultrasonic transducer at the distal end of said ultrasound catheter to the at least one COVID-19-damaged distal lung region in pulses of predetermined duration and predetermined inter-pulse spacing effective to induce mechanical stress in alveoli and lung epithelial layers in the at least one COVID-19 damaged distal lung region.

2. The method of claim 1 wherein said ultrasound catheter is steerable, the advancing of said ultrasound catheter including introducing said ultrasound catheter through said elongate introducer instrument, wherein an optical fiber is inserted in a central lumen of the ultrasound catheter for guidance.

3. The method of claim 1 wherein the ultrasound catheter is provided with depth markings, further comprising:
imaging a treatment site prior to the inserting of said distal end portion of the elongate introducer instrument; and
determining a length of insertion of the ultrasound catheter in accordance with images of the treatment site,
the advancing of said ultrasound catheter being terminated upon attainment of the determined length of insertion of the ultrasound catheter.

4. The method of claim 1 wherein the elongate introducer instrument is a steerable sheath containing an optical imaging fiber for visualization, the advancing of the ultrasound catheter including:
first inserting into the subject the steerable sheath containing the optical imaging fiber for visualization;
positioning a distal tip of the steerable sheath distal to the main bronchial bifurcation of the subject; and
replacing the optical imaging fiber with the ultrasound catheter.

5. The method of claim 1, further comprising using the elongate introducer instrument to place a guidewire, the advancing of the ultrasound catheter including advancing the ultrasound catheter over the guidewire after the elongate introducer instrument has been withdrawn.

6. The method of claim 1, further comprising operating the ultrasonic transducer in a receive mode to detect and prevent improper coupling of the balloon and the bronchial wall.

7. The method of claim 1, further comprising operating the ultrasonic transducer in a receive mode and detecting distance of an esophagus from the balloon to avoid esophageal injury in case of the esophagus containing air.

8. A COVID-19 treatment method comprising:
inserting a distal end portion of an ultrasound catheter into a bronchial tree of a patient diagnosed as having at least one COVID-19 damaged distal lung region, the inserting of said distal end portion including disposing said distal end portion in a distal portion of the bronchial tree proximate the at least one COVID-19 damaged distal lung region;
operating said ultrasound catheter to place an ultrasonic transducer at a distal end of said ultrasound catheter into effective ultrasound-transmitting contact with a bronchial wall of the patient proximate the at least one COVID-19 damaged distal lung region; and
thereafter energizing said ultrasonic transducer to apply circumferential focused or unfocused ultrasound energy to the at least one COVID-19 damaged distal lung region of the patient via the bronchial wall, in pulses of predetermined duration and predetermined inter-pulse spacing effective to induce mechanical stress in alveoli and lung epithelial layers in the at least one COVID-19 damaged distal lung region.

9. The method of claim 8 wherein said ultrasound catheter is steerable, the inserting of said distal end portion of said ultrasound catheter including introducing said distal end portion through an elongate introducer instrument, wherein an optical fiber is inserted in a central lumen of the ultrasound catheter for guidance.

10. The method of claim 9 wherein the elongate introducer instrument is a steerable sheath containing an optical imaging fiber for visualization, the inserting of said distal end portion of the ultrasound catheter including:
first inserting into the patient the steerable sheath containing the optical imaging fiber for visualization;
positioning a distal tip of the steerable sheath distal to a main bronchial bifurcation of the patient; and
replacing the optical imaging fiber with the ultrasound catheter.

11. The method of claim 9, further comprising using the elongate introducer instrument to place a guidewire, the advancing of the ultrasound catheter including advancing the ultrasound catheter over the guidewire after the elongate introducer instrument has been withdrawn.

12. The method of claim 8 wherein the ultrasound catheter is provided with depth markings, further comprising:
imaging a treatment site prior to the inserting of said distal end portion of the ultrasound catheter; and
determining a length of insertion of the ultrasound catheter in accordance with images of the treatment site,
the advancing of said ultrasound catheter being terminated upon attainment of the determined length of insertion of the ultrasound catheter.

13. The method of claim 8 wherein the ultrasonic transducer is disposed inside a liquid-filled balloon at the distal end of said ultrasound catheter, further comprising operating the ultrasonic transducer in a receive mode to detect and prevent improper coupling of the balloon and the bronchial wall.

14. The method of claim 8 wherein the ultrasonic transducer is disposed inside a liquid-filled balloon at the distal end of said ultrasound catheter, further comprising operating the ultrasonic transducer in a receive mode and detecting distance of an esophagus of the patient from the balloon to avoid esophageal injury.

15. A COVID-19 treatment method comprising:
providing an ultrasound apparatus;
placing said ultrasound apparatus into effective ultrasound-transmitting contact with a patient diagnosed as having at least one COVID-19 damaged distal lung region;
thereafter operating said ultrasound apparatus to apply focused or unfocused ultrasound energy to the at least one COVID-19 damaged distal lung region of the patient with a waveform effective to induce mechanical stress in alveoli and lung epithelial layers in the at least one COVID-19 damaged distal lung region.

* * * * *